(12) United States Patent
Korzinov et al.

(10) Patent No.: US 7,996,075 B2
(45) Date of Patent: Aug. 9, 2011

(54) MONITORING PHYSIOLOGICAL ACTIVITY USING PARTIAL STATE SPACE RECONSTRUCTION

(75) Inventors: Lev Korzinov, San Diego, CA (US);
Michael Kremliovsky, Poway, CA (US)

(73) Assignee: CardioNet, Inc., Conshohocken, PA (US)

( * ) Notice: Subject to any disclaimer, the term of this patent is extended or adjusted under 35 U.S.C. 154(b) by 758 days.

(21) Appl. No.: 11/081,401

(22) Filed: Mar. 15, 2005

(65) Prior Publication Data
US 2006/0084881 A1   Apr. 20, 2006

Related U.S. Application Data

(60) Provisional application No. 60/633,320, filed on Dec. 3, 2004, provisional application No. 60/620,864, filed on Oct. 20, 2004.

(51) Int. Cl.
*A61B 5/0452* (2006.01)
(52) U.S. Cl. .......................... 600/515; 600/509
(58) Field of Classification Search .......... 600/508–523; 607/5–30
See application file for complete search history.

(56) References Cited

U.S. PATENT DOCUMENTS

| | | | |
|---|---|---|---|
| 4,646,754 A | 3/1987 | Seale | |
| 5,047,930 A | 9/1991 | Martens et al. | |
| 5,299,118 A | 3/1994 | Martens et al. | |
| RE34,663 E | 7/1994 | Seale | |
| 5,522,393 A | 6/1996 | Phillips et al. | |
| 5,560,367 A | 10/1996 | Haardt et al. | |
| 5,596,993 A | 1/1997 | Oriol et al. | |
| 5,609,158 A | 3/1997 | Chan | |
| 5,645,069 A | 7/1997 | Lee | |
| 5,810,014 A | 9/1998 | Davis et al. | |
| 5,827,195 A | 10/1998 | Lander | |
| 5,921,937 A | 7/1999 | Davis et al. | |
| 5,957,855 A | 9/1999 | Oriol et al. | |
| 6,024,701 A | 2/2000 | Almog | |
| 6,028,428 A | 2/2000 | Cunningham et al. | |
| 6,069,975 A | 5/2000 | Lehmann et al. | |
| 6,076,015 A | 6/2000 | Hartley et al. | |
| 6,161,042 A | 12/2000 | Hartley et al. | |
| 6,216,031 B1 | 4/2001 | Findeis et al. | |
| 6,269,263 B1 | 7/2001 | Ohnishi et al. | |
| 6,278,961 B1 | 8/2001 | Kadtke et al. | |
| 6,340,346 B1 | 1/2002 | Almog et al. | |

(Continued)

FOREIGN PATENT DOCUMENTS

CN    2569743 Y    9/2003

(Continued)

OTHER PUBLICATIONS

Coast, D.A. et al., "An Approach to Cardiac Arrhythmia Analysis Using Hidden Markov Models", IEEE Transactions on Biomedical Engineering, vol. 37, Issue 9, Sep. 1990.—pp. 826-836.

(Continued)

*Primary Examiner* — Scott M Getzow
(74) *Attorney, Agent, or Firm* — Fish & Richardson P.C.

(57) ABSTRACT

Systems and techniques relating to monitoring physiological activity using partial state space reconstruction. In general, in one aspect, a partial state space is produced using an orthogonal, frequency-independent transform, such as Hilbert transform. The partial state space can then be analyzed using state space techniques to identify physiological information for the biological system. The described techniques can be implemented in a distributed cardiac activity monitoring system, including a cardiac monitoring apparatus, and a QRS detector thereof.

51 Claims, 6 Drawing Sheets

U.S. PATENT DOCUMENTS

| | | | |
|---|---|---|---|
| 6,368,283 | B1 | 4/2002 | Xu et al. |
| 6,370,437 | B1 | 4/2002 | Carter et al. |
| 6,377,843 | B1 | 4/2002 | Naydenov et al. |
| 6,381,559 | B1 | 4/2002 | Huang |
| 6,400,996 | B1 | 6/2002 | Hoffberg et al. |
| 6,401,057 | B1 | 6/2002 | Kadtke et al. |
| 6,442,421 | B1 | 8/2002 | Le Van Quyen et al. |
| 6,463,326 | B1 | 10/2002 | Hartley et al. |
| 6,507,749 | B1 | 1/2003 | Macgowan et al. |
| 6,507,754 | B2 | 1/2003 | Le Van Quyen et al. |
| 6,537,233 | B1 | 3/2003 | Rangayyan et al. |
| 6,561,986 | B2 | 5/2003 | Baura et al. |
| 6,564,176 | B2 | 5/2003 | Kadtke et al. |
| 6,569,101 | B2 | 5/2003 | Quistgaard et al. |
| 6,640,145 | B2 | 10/2003 | Hoffberg et al. |
| 6,651,025 | B1 | 11/2003 | Drepper |
| 6,728,691 | B1 | 4/2004 | Neuneier et al. |
| 6,731,990 | B1 | 5/2004 | Carter et al. |
| 6,732,064 | B1 | 5/2004 | Kadtke et al. |
| 6,735,466 | B1 | 5/2004 | Haghighi-Mood |
| 6,738,734 | B1 | 5/2004 | Huang |
| 6,950,702 | B2 | 9/2005 | Sweeney |
| 2001/0014776 | A1 | 8/2001 | Oriol et al. |
| 2002/0095099 | A1 | 7/2002 | Quyen et al. |
| 2003/0009399 | A1 | 1/2003 | Boerner |
| 2003/0065633 | A1 | 4/2003 | Nueneier et al. |
| 2003/0105499 | A1 | 6/2003 | Hartley et al. |
| 2003/0166995 | A1 | 9/2003 | Jansen |
| 2003/0233050 | A1 | 12/2003 | Haghighi-Mood et al. |
| 2004/0260169 | A1* | 12/2004 | Sternnickel ............... 600/409 |
| 2007/0100213 | A1 | 5/2007 | Dossas et al. ............. 600/300 |
| 2007/0219453 | A1 | 9/2007 | Kremliovsky et al. |

FOREIGN PATENT DOCUMENTS

| | | |
|---|---|---|
| WO | WO9743721 | 11/1997 |
| WO | WO03003905 | 1/2003 |
| WO | WO 03/071945 | 9/2003 |
| WO | WO 2006/044919 | 4/2006 |

OTHER PUBLICATIONS

Daskalov, I.K., et al., "Automatic Detection of the Electrocardiogram T-Wave End", Medical & Biological Engineering & Computing, vol. 37, Issue 3, May 1999, pp. 348-353.

Daskalov, I.K., et al., "Electrocardiogram Signal Preprocessing for Automatic Detection of QRS Boundaries", Medical Engineering & Physics 21, 1999, pp. 37-44.

Goldberger, A. L. et al., "QRS Duration Measurement Using High-Frequency Electrocardiography: Applications and Limitations of a New Technique", Computers and Biomedical Research, vol. 15, Issue 5, Oct. 1982, pp. 474-484.

Gritzali, F. et al., "Detection of the P and T waves in an ECG", Computers and Biomedical Research, vol. 22, Issue 1, Feb. 1989, pp. 83-91.

Hamilton, P. S. et al., "Quantitative Investigation of QRS Detection Rules Using the MIT/BIH Arrhythmia Database", IEEE Transactions on Biomedical Engineering, vol. BME-33, Issue 12, Dec. 1986, pp. 1157-1165.

Kemmelings, J. G. C. et al., "Automatic QRS Onset and Offset Detection for Body Surface QRS Integral Mapping of Ventricular Tachycardia", IEEE Transactions on Biomedical Engineering, vol. 41, Issue 9, Sep. 1994. pp. 830-836.

Laguna, P. et al., "Automatic Detection of Wave Boundaries in Multilead ECG Signals: Validation with the CSE Database", Computers and Biomedical Research, vol. 27, Issue 1, Feb. 1994, pp. 45-60.

Laguna, P. et al., "New Algorithm for QT Interval Analysis In 24-Hour Holter ECG: Performance and Applications", Medical & Biological Engineering & Computing, vol. 28, Issue 1, Jan. 1990, pp. 67-73.

Li, C. et al., "Detection of ECG Characteristic Points Using Wavelet Transforms", IEEE Transactions on Biomedical Engineering, vol. 42, Issue 1, Jan. 1995, pp. 21-28.

Sun, Yan et al., "Characteristic Wave Detection in ECG Signal Using Morphological Transform", BMC Cardiovascular Disorders (http://www.biomedcentral.com/content/pdf/1471-2261-5-28.pdf), Sep. 2005, pp. 1-7.

Willems, J. L. et al., "Influence Of Noise on Wave Boundary Recognition by ECG Measurement Programs. Recommendations for Preprocessing", Computers and Biomedical Research, vol. 20, Issue 6, Dec. 1987, pp. 543-562.

C. R. Meyer et al., "Electrocardiogram baseline noise estimation and removal using cubic splines and state-space computation techniques", Computers and Biomedical Research, vol. 10, pp. 459-470, 1977.

S. Haykin, Editor, "Nonlinear Methods of Spectral Analysis",Topics in Applied Physics, vol. 34, Springer-Verlag, 1979.

S. M. Kay et al., "Spectrum Analysis—A Modern Perspective", Proceedings of the IEEE, vol. 69, No. 11, Nov. 1981.

N. Thrane, Ph.D., "The Hilbert Transform", in Technical Review No. 3—1984.

B. D. Rao et al., "Model based Processing of Signals: A State Space Approach", Proc. IEEE, vol. 80, pp. 283-309, Feb. 1992.

D. Benitez et al. "The use of the Hilbert transform in ECG signal analysis", Computers in Biology and Medicine 31 (2001) 399-406.

"Hilbert Transform, Analytic Signal and the Complex Envelope", Signal Processing & Simulation Newsletter, http://www.complextoreal.com/tcomplex.htm.

"The QT Interval" 12-LEAD ECG's—A "Web Brain" for Easy Interpretation, http:////medinfo.ufl.edu/~ekg/QT%20interval.html.

Jeekai & Partners, Translation of Office Action mailed May 23, 2008 in Chinese Patent Application No. 2005-80040134.5, which corresponds to U.S. Appl. No. 11/081,401, to be published by the U.S. Patent and Trademark Office (11 pages).

Scott M. Getzow, International Search Report and Written Opinion mailed May 19, 2006 in PCT Application No. PCT/US05/37492, which corresponds to U.S. Appl. No. 11/081,401, to be published by the U.S. Patent and Trademark Office (8 pages).

Australian Government IP Australia, Examination Report, mailed Sep. 15, 2008, 3 pages.

Bray, Mark-Anthony, "Use of Topological Charge to Determine Filament Location and Dynamics in a Numerical Model of Scroll Wave Activity," *IEEE Transactions on Biomedical Engineering*, 49(10):1086-1093 (Oct. 2002), 8 pages.

Canadian Patent Office, Application No. 2,584,503, in Office Action dated Feb. 16, 2009, 6 pages.

Song-Kai et al., "The Real-Time Detection of QRS-Complex using the Envelop of ECG", IEEE Engineering in Medicine and Biology Society, 10th Annual International Conference, 1988, 1 page.

Bennet, Bill, Attorney for Pizzeys, in Australian Patent Application No. 2005295313, International Filing Date of Oct. 18, 2005, response filed on May 27, 2009, 25 pages, (to be published by USPTO).

Hunter, William E., Attorney for Fish & Richardson, in Canadian Patent Application No. 2,584,503, International Filing Date of Oct. 18, 2005, instructions to Foreign Associate for response to Office Action dated Mar. 24, 2009, 12 pages (to be published by the USPTO).

Weber, Myriam, Authorized Officer, European Patent Office, in International Application No. PCT/US2007/063916, International Search Report, mailed Apr. 3, 2008, 16 pages, (to be published by the USPTO).

Meyer, M. et al., "Stability of Heartbeat Interval Distributions in Chronic High Altitude Hypoxia," Oct.-Dec. 1998, Intergrative Physiological and Behavioral Science, 33(4):344-362, 43 pages.

Australian Government IP Australia, to be published by USPTO, Examination Report dated Aug. 7, 2009, 2 pages.

Bhattacharya et al., "Universality in the brain while listening to music," Apr. 2001, Proceedings Royal Society London B., 268:2423-2433, 11 pages.

Electronic Records Administration, in Australian Patent Application Serial No. 2005295313, filed Oct. 18, 2005, Notice of Acceptance, mailed Dec. 10, 2009, 3 pages, to be published by the USPTO.

Canadian Intellectual Property Office, Application No. 2584503, filed Oct. 18, 2002, in Office Action, mailed Feb. 8, 2011, 4 pages.

European Patent Office, PCT Application No. PCT/US2005/037492, filed Oct. 18, 2005, in International Search Report and Written Opinion mailed Jun. 16, 2010, 8 pages to be published by USPTO.

Owis, I Mohammed, "Study of Features Based on Nonlinear Dynamical Modeling in ECG Arrhythmia Detection and Classification", ISBN: 0018-9294, IEEE Transactions on vol. 49, Issue 7, Jul. 1, 2002, Section 2-5.

* cited by examiner

MONITORING PHYSIOLOGICAL ACTIVITY USING PARTIAL STATE SPACE RECONSTRUCTION

CROSS REFERENCE TO RELATED APPLICATIONS

This application claims the benefit of the priority of U.S. Provisional Application Ser. No. 60/620,864, filed Oct. 20, 2004 and entitled "MONITORING PHYSIOLOGICAL ACTIVITY USING PARTIAL STATE SPACE RECONSTRUCTION"; and this application claims the benefit of the priority of U.S. Provisional Application Ser. No. 60/633,320, filed Dec. 3, 2004 and entitled "MONITORING PHYSIOLOGICAL ACTIVITY USING PARTIAL STATE SPACE RECONSTRUCTION".

BACKGROUND

The present application describes systems and techniques relating to monitoring physiological activity of an organism, for example, performing QRS detection on a cardiac signal obtained from a person.

The electrical activity of various organs, such as the heart or brain, can be monitored, and this electrical activity can be analyzed to look for patterns that may assist in diagnosing various conditions. For example, the electrical activity of the heart can be monitored to track various aspects of the functioning of the heart. Given the volume conductivity of the body, electrodes on the body surface or beneath the skin can display potential differences related to this activity. Anomalous electrical activity can be indicative of disease states or other physiological conditions ranging from benign to fatal.

Cardiac monitoring devices can sense the cardiac electrical activity of a living being and identify heart beats. Frequently, identification of heart beats is performed by identifying the R waves in the QRS complex, as can be seen in an electrocardiogram (ECG). The R wave represents ventricular depolarization. The typically large amplitude of this wave in the QRS complex is useful in identifying a heart beat. Traditional automated ECG signal analysis tools typically rely on correlation-based template matching and a number of empirical decision rules that are optimized for certain ECG databases. Many techniques have been developed for performing QRS detection, but further improvements are desirable.

SUMMARY

The present disclosure includes systems and techniques relating to monitoring physiological activity using partial state space reconstruction. In general, in one aspect, a partial reconstruction of a state space for a biological system can be produced using a frequency-independent transform, such as Hilbert transform, which produces a transformed signal that is mathematically orthogonal to a physiological signal. The idea of extracting dynamical information from a partially reconstructed state space relies on the observation that full reconstruction does not necessarily improve understanding of the most important features of the physiological activity. The lower dimensional partial reconstruction often contains all the key features required to extract dynamical properties of the physiological system. The partial state space can then be analyzed using state space techniques to identify physiological information. These techniques can be implemented in a distributed cardiac activity monitoring system, including a cardiac monitoring apparatus, and a QRS detector thereof.

One or more of the following advantages may be provided. Dynamical features of the heart can be better and more naturally represented in higher dimensional state space. Hilbert transform can be easily implemented in a form of digital filter with a minimal distortion for spectral characteristic of the underlying signal. Reliable classification of heart beats can be based on their morphology in a higher dimensional space as opposed to a conventional time series representation. For example, ventricular beats can be readily distinguished from normal beats by automated procedures. Moreover, this classification can be accurately performed even when there are a smaller number of leads in the cardiac monitoring system, which can provide advantages in terms of reduced data storage and extended monitoring applications.

Electrical signals obtained from a biological system, such as the heart, are a measure of electric potential created by the biological system, and thus these signals are only representative of the real dynamics of the biological system. The present systems and techniques can enable an automated process to perform what can be considered an inverse problem, similar to what a clinician or physician does when looking at an ECG time series, going from the obtained signals back to the system dynamics, and thereby figuring out what happened in the heart to cause the lead signals to behave as observed.

State space transformation allows a physiological signal to be represented in a very general/invariant form, which can avoid peculiarities associated with particular anatomic and/or electrophysiological features of the subjects. In general, noise has increasingly different/irregular dynamical behavior in higher dimensional space, and thus its detection and estimation becomes an easier task. The risk of false positives, false negatives, or both can be reduced. Using Hilbert transform in combination with state space techniques can result in substantial improvements in identification of signal features. Dynamical quantities of the signal can be calculated, and subsequent analysis operations can be based on these dynamical quantities. Monitoring devices can be improved by using automated analysis based on dynamical quantities to detect when an arrhythmia is happening with a high degree of accuracy and high sensitivity. Effective automation of the detection and diagnosis of heart arrhythmia can thus be achieved using the very nature of the heart dynamical behavior.

The details of one or more embodiments are set forth in the accompanying drawings and the description below. Other features and advantages will become apparent from the description, the drawings, and the claims.

DETAILED DESCRIPTION

The systems and techniques described here enable partial reconstruction of heart dynamics from one- and two-lead systems. In general, the approach described here is based on the fact that an acquired electrical signal, such as an ECG signal, is a representation, or a projection, of the electrical activity of a biological system (e.g., the heart) onto some lead system. Reconstructing the dynamics of the heart from the available leads' signals can result in more accurate diagnosis of the heart's electrical activity. Partial reconstruction of the heart's dynamics can be performed using only a couple of leads. The systems and techniques described below (e.g., a Mobile Cardiac Outpatient Telemetry System) can result in improved diagnostics without requiring significant additional computational resources. Other advantages can include a more precise detection of fiducial points, used for such calculations as QRS width and QT interval, a more accurate ventricular morphology analysis, and improved stability of the detection algorithm in the presence of noise.

Figure 1:
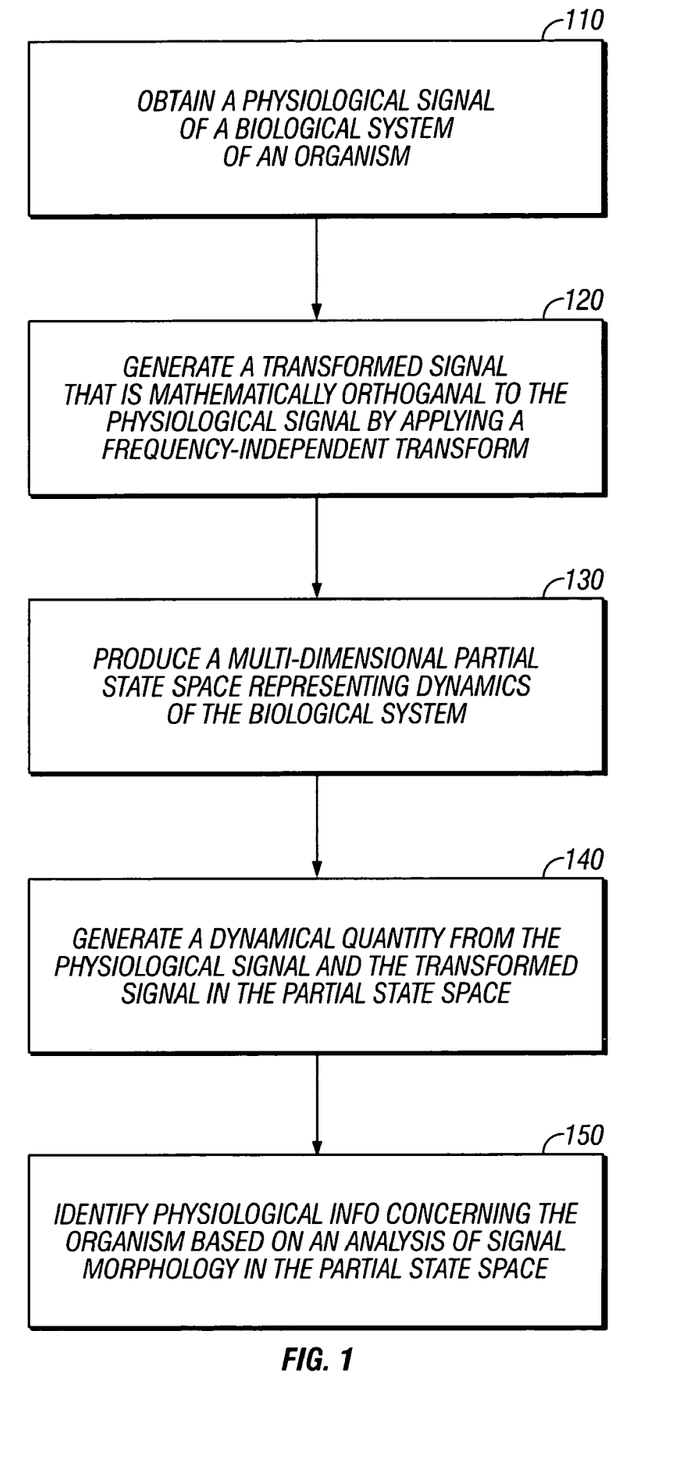
FIG. 1 is a flow chart illustrating monitoring of physiological activity using partial state space reconstruction.

FIG. 1 is a flow chart illustrating monitoring of physiological activity using partial state space reconstruction. A physiological signal of a biological system of an organism is obtained at 110. The physiological signal can be a cardiac signal, such as an ECG signal, a brain signal, such as an electroencephalogram (EEG) signal, a respiratory signal, a blood pressure signal, or other signals from an organism. The signal(s) can be obtained directly, such as by monitoring heart activity of a human patient as described further below, or the signal(s) can be obtained indirectly from another device or system. For example, the signal processing and analysis described herein can be performed in real-time as the signals are acquired and/or on stored signals retrieved from a database or other electronic storage devices.

A transformed signal is generated by applying a frequency-independent transform (e.g., a digital version of Hilbert transform) at 120. The transformed signal is mathematically orthogonal to the physiological signal, and the transform is frequency-independent in that it does not favor or amplify some frequencies of the signal over others. This frequency-independence can be particularly useful in analyzing biological signals, such as ECG data, where the frequency spectrum can easily cover a wide range of frequencies. For example, the heart's frequency spectrum can include frequencies as low as 1 hertz and as high 100 hertz.

Moreover, the frequency-independent transform can be a generally noise insensitive transform, such as Hilbert transform. This can be of tremendous value when analyzing signals sensed from biological systems, where the noise component of the signal may be significant. The Hilbert transform can be especially useful in this context, despite that fact that Hilbert transform imposes potential limits on what might otherwise be considered a preferred approach of full scale embedding for the biological system. The present inventors have recognized that a partial state space approach is nonetheless extremely useful given the typical dominance of a few major wave forms in the real-world, sensed physiological signals.

A multi-dimensional partial state space is produced from the physiological signal and the transformed signal at 130. The partial state space is a partial reconstruction of a potential full state space for the biological system, and the full state space represents the dynamics of the biological system. Employing state space techniques, which are specific to the state space representation, to analyze biological system activity has been found to be quite effective, even when working only in a partial state space (i.e., a lower dimensional space).

Even a two dimensional partial state space (the original signal plus its Hilbert transform, with the third dimension of time being implicit) has been found highly effective in QRS detection as described below; and using a lower dimensional space can have significant advantages in terms reducing the complexity of automated analysis (e.g., in some implementations, only a single lead and thus only a single input signal are needed). Using state space techniques on a partial state space to identify physiological information can be very effective in practice because the partial state space retains many properties of the original signal, while also adding properties specific to the state space representation. For example, noise in the original signal tends to have increasingly different/irregular dynamical behavior in higher dimensional space, and thus its detection and estimation can become an easier task in a physiological monitoring device or monitoring station in communication with such a device.

Obtaining the physiological signal can involve receiving an electrically-sensed time series $x(t)$, generating higher dimensional signal can involve applying Hilbert (H) transform to the time series $x(t)$ to obtain $H(x(t))$, and producing the multi-dimensional partial state space can involve considering $x(t)$ and $H(x(t))$ together as components of a state vector. These two variables, $x(t)$ and $H(x(t))$, form a simple partial state space. Such procedure is also called embedding of $x(t)$ into (partial) state space. For an implementation using multiple source signals (e.g., a multi-lead ECG input), $x(t)$ is a multi-dimensional vector, in which case, both $x(t)$ and $H(x(t))$ are vectors, and the partial state space has dimensions equal to twice that of $x(t)$.

One or more dynamical quantities can be generated from the physiological signal and the transformed signal at 140. If a point in a state space describes particular dynamical state, dynamical quantities describe how this state evolves in space and time, for example, how physiological state evolves from point to point. For example, the generated dynamical quantities can be nonlinear transformations of $x(t)$ and $H(x(t))$ in state space, excepting simple linear combinations of amplitude and phase. In general, a dynamical quantity can be used to characterize evolution of a dynamical state of the biological system.

Physiological information concerning the organism is identified, at 150, based on an analysis of signal morphology in the multi-dimensional partial state space. Identifying the physiological information can involve detecting a physiological occurrence for the biological system based on a dynamical quantity, which is a value derived from the combination of physiological and transformed signals as mentioned above. Additionally, identifying the physiological information can involve assessing multiple dynamical quantities with respect to one or more predefined physiological aspects of the biological system.

Figure 2:
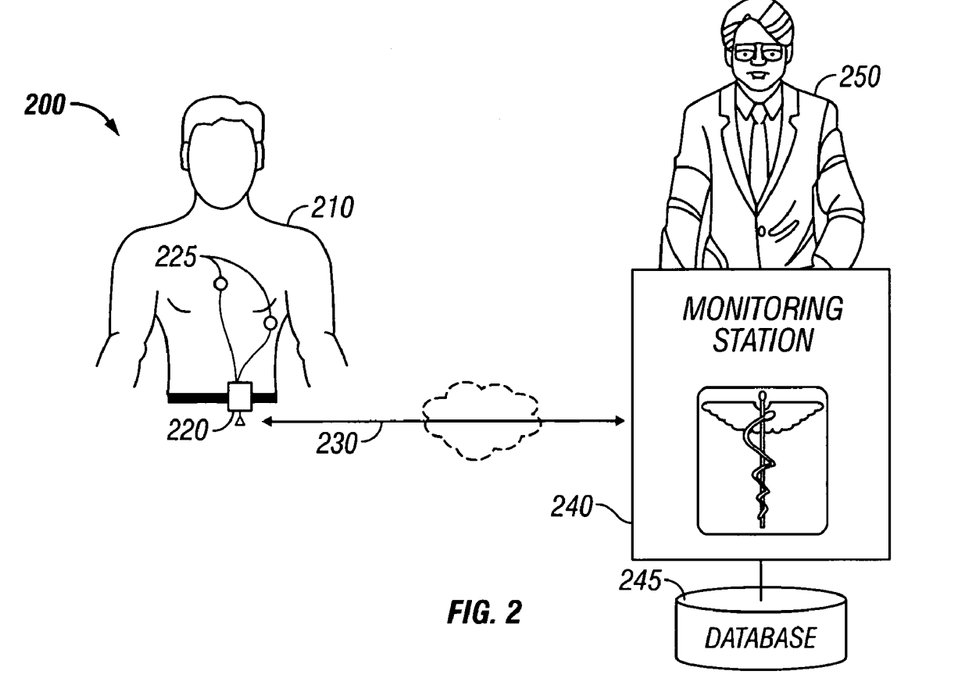
FIG. 2 illustrates a distributed cardiac activity monitoring system in which a cardiac signal is monitored for medical purposes.

FIG. 2 illustrates a distributed cardiac activity monitoring system 200 in which a cardiac signal is monitored for medical purposes. An organism 210 (e.g., a human patient, including potentially a healthy patient for whom cardiac monitoring is nonetheless deemed appropriate) has a cardiac monitoring apparatus 220 configured to obtain cardiac signals from the patient's heart. The cardiac monitoring apparatus 220 can be composed of one or more devices, such as a processing device and a sensing device. The sensing device can include two independent leads 225, which can receive electrical signals through body surface electrodes as shown (e.g., silver/silver chloride electrodes, which can be positioned at defined locations to aid in monitoring the electrical activity of the heart). As used herein, the term "lead" should be understood as including both a device that is subject to a potential difference that yields a voltage signal, such as an electrode that produces an ECG signal, and a conductor that forms a signal path to any signal amplifier used in the apparatus 220.

The cardiac monitoring apparatus 220 can communicate with a monitoring station 240 (e.g., a computer in a monitoring center) via a communications channel 230. The cardiac monitoring apparatus 220 can include one or more sensing, calibration, signal processing, control, data storage, and transmission elements suitable for generating and processing the cardiac signal, as well as for relaying all or a portion of the cardiac signal over the communications channel 230. The communications channel 230 can be part of a communications network and can include any suitable medium for data transmission, including wired and wireless media suitable for carrying optical and/or electrical signals. Wireless communications by the apparatus 220 can employ a suitable antenna as illustrated.

The cardiac monitoring apparatus 220 can communicate sensed cardiac signals, cardiac event information (e.g., real-time heart rate data), and additional physiological and/or other information to the monitoring station 240. The cardiac monitoring apparatus 220 can include an implantable medical device, such as an implantable cardiac defibrillator and an associated transceiver or pacemaker and an associated transceiver, or an external monitoring device that the patient wears or even stationary installed. Moreover, the cardiac monitoring apparatus 220 can be implemented using, for example, the CardioNet Mobile Cardiac Outpatient Telemetry (MCOT) device, which is commercially available and provided by CardioNet, Inc of San Diego, Calif.

The monitoring station 240 can include a receiver element for receiving transmitted signals, as well as various data processing and storage elements for extracting and storing information carried by transmissions regarding the state of the individual 210. The monitoring station 240 can be located in the same general location (e.g., in the same room, building or health care facility) as the monitoring apparatus 220, or at a remote location. The monitoring station 240 can include a display and a processing system, and a system operator 250 (e.g., a doctor or a cardiovascular technician) can use the monitoring station 240 to evaluate physiological data received from the cardiac monitoring apparatus 220. The system operator 250 can use the monitoring station 240 to change operational settings of the cardiac monitoring apparatus 220 remotely during active cardiac monitoring of the person 210.

Moreover, the cardiac monitoring apparatus 220 and/or the monitoring station 240 can use the systems and techniques described herein to identify physiological information concerning the person 210. This can include signal processing and analysis on both an actively received signal and prior signals stored in a database 245. For example, historical signal information for a person can be used in conjunction with the systems and techniques described herein to improve analysis of currently acquired signals, and can facilitate heart beat classification and characterization of physiological conditions, which can assist a clinician or physician in making an appropriate diagnosis and prescribing an appropriate treatment.

Figure 3:
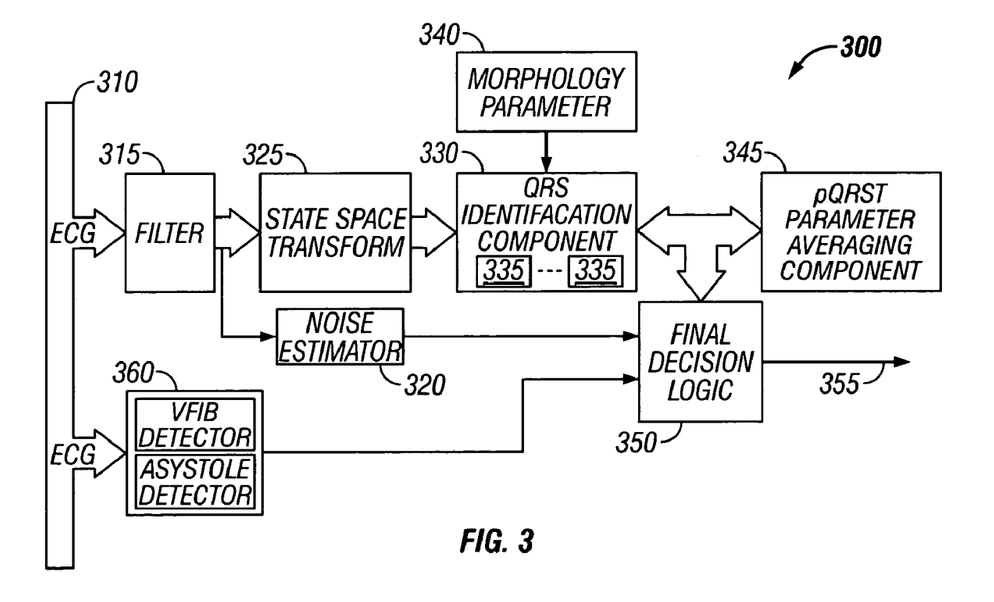
FIG. 3 is a block diagram illustrating an example QRS detector in a cardiac monitoring apparatus.

FIG. 3 is a block diagram illustrating an example QRS detector 300 in a cardiac monitoring apparatus. An ECG input element 310 includes a split output that provides an ECG signal to two processing paths within the QRS detector. A filter 315 operates on a first of these ECG signals to clean the signal as needed for later analytical processing. The filter 315 can be a filter bank, which can include a baseline shift remover, and one or more band pass filters configured to clean the ECG signal for various aspects of the later processing; the filter bank 315 can also split the ECG signal into separate signals for later parallel processing and/or include an analog-to-digital converter.

Output of the filter 315 can be provided to a noise estimator 320 and a state space transformation component 325. The state space transformation component 325 can generate a partial state space as described, such as by applying Hilbert transform directly to the ECG signal and providing both the ECG signal and the transformed ECG signal to a QRS identification component 330. It should be noted that applying the Hilbert transform "directly to" the ECG signal as shown (the intermediate filtering is not considered to negate this direct application of the Hilbert transform as such filtering does not constitute intermediate analytical processing) can have significant advantages in combination with the state space analysis techniques described; Hilbert transform can be applied at the front-end of the algorithm, rather than to some derivative of the cardiac signal. In addition, the state space transformation component 325 can effect noise cancellation in the process of transforming the signal, which can be a result of the partial state space the signal is transformed into.

The QRS identification component 330 is responsive to the output of the state-space transformation component 325 and includes one or more dynamical quantity calculators 335, such as described further below. The QRS identification component 330 can perform signal analysis in the partial state space based on morphology parameters 340 provided to it, and the QRS identification component 330 can be coupled with both a pQRST parameter averaging component 345 and final QRS decision logic 350.

The final QRS decision logic 350 can base its QRS detector output 355 on input received from the QRS identification component 330, the pQRST parameter averaging component 345, and the noise estimator 320. This can include detecting heart beats, and can also include detecting a physiological occurrence by assessing one or more dynamical quantities with respect to one or more predefined physiological aspects of the human heart (e.g., classifying heart beats as normal or abnormal based on ventricular depolarization). In addition, the final decision logic 350 can also base its QRS detector output 355 on input received from an arrhythmia identification component 360 coupled with the split output of the ECG input 310. The arrhythmia identification component 360 can include a ventricular or atrial fibrillation detector and an asystole detector, which can employ various known techniques for identifying ventricular fibrillation and the absence of heart contractions.

The QRS detector 300 can be implemented in the monitoring station 240 and/or in the cardiac monitoring apparatus 220, the various components of which can be implemented as analog or digital components. The QRS detector 300 can be a real-time QRS detector that identifies successive QRS complexes and determines the beat-to-beat timing in real time (i.e., output data is generated directly from live input data). The beat-to-beat timing (RR-interval) can be determined by measuring times between successive R-waves. The QRS detector output 355 can be provided to additional logic, which can include logic to determine if an abnormal T wave potentially is occurring based on signal morphology analysis, an atrial fibrillation/atrial flutter (AF) detector, AF decision logic, and an event generator. Moreover, the sensed cardiac signal, or portions thereof, can be sent to a monitoring station, periodically, upon being interrogated and/or in response to identified events/conditions.

Figure 4:
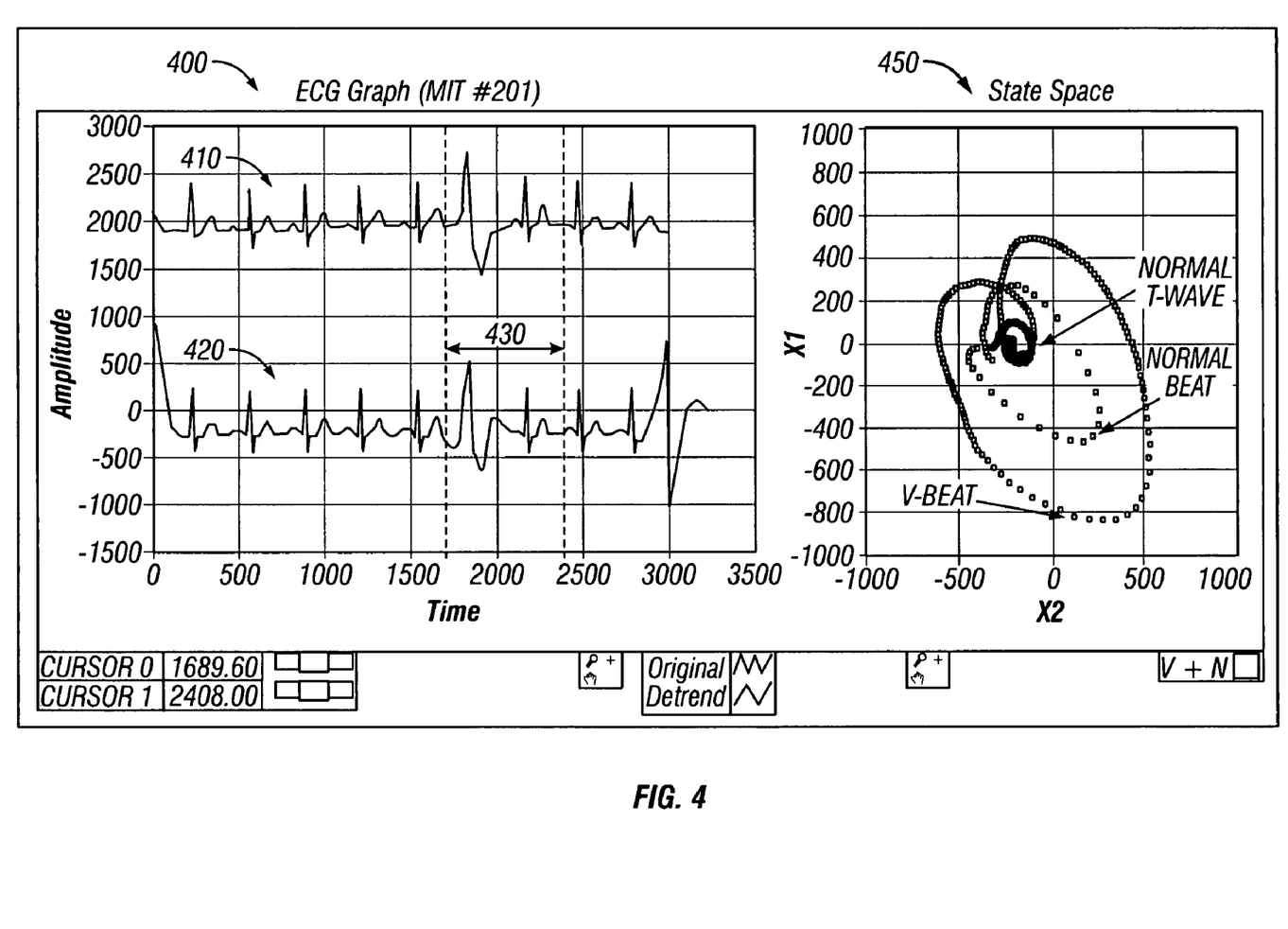
FIGS. 4, 8A, 8B and 8C illustrate a state space approach to beat classification based on ventricular depolarization using analytical signal reconstructed using Hilbert transform.

FIG. 4 illustrates a state space approach to beat classification based on ventricular depolarization. A first graph 400 shows an ECG signal 410 and its bandpass filtered version 420, with amplitude being the vertical axis and time being the horizontal axis. The heart cycle includes the traditionally recognized waveforms: the P wave, the QRS complex, the T wave, and the U wave. An abnormal heart beat is included in a time window 430, and a second graph 450 shows this abnormal heart beat presented in a partial state space.

The partial state space presents signal amplitude on the vertical axis and the Hilbert transform of the signal on the horizontal axis. Time is on the Z axis, which is perpendicular to the plane of the page. Thus, the time window 430 controls how many signal points are overlaid within the presented state space representation, and time is represented by the order in which the points are placed on the graph 450.

As can be seen, a normal beat is clearly differentiable from an abnormal Ventricular beat (e.g., by calculating how many points it takes to go through the big loops, which represent the QRS complex; the small loops shown are the T waves). Using this state space approach to cardiac signal analysis can be much more robust in practice than traditional analysis of a cardiac time series, because the state space approach is much less likely to be confused by a signal on any particular axis (note that the heart can be in different positions in the chest and/or relative to the lead). Although one or more graphs such as this can be employed in a user interface of a system, the main purpose of this graph is to illustrate the advantages of analyzing signal morphology in a multi-dimensional partial state space. In many applications, this analysis is expected to be fully automated, especially when the embedding space used has four or more spatial dimensions (plus the temporal dimension), which can be difficult for a human to visualize and understand.

Figure 5:
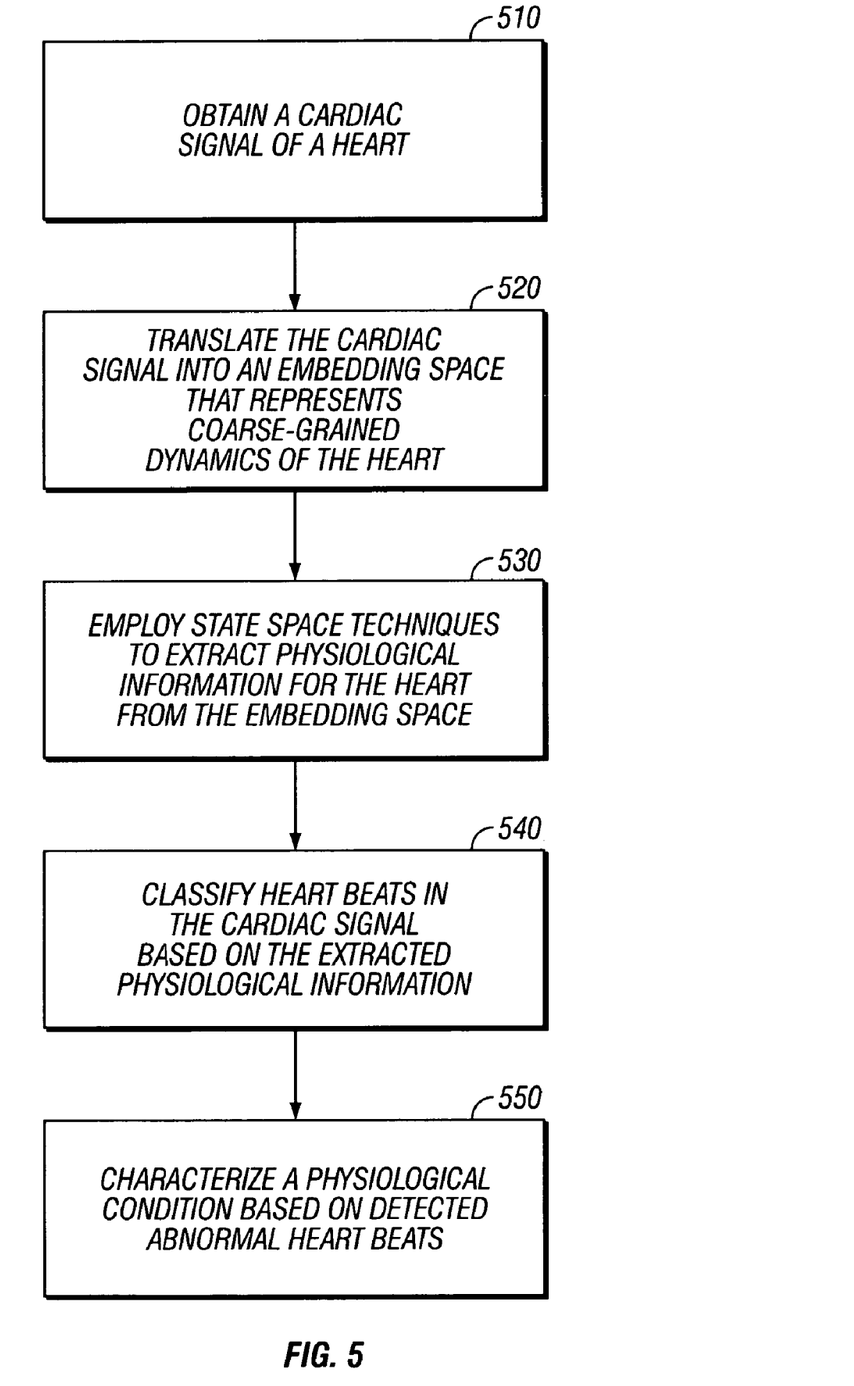
FIG. 5 is a flow chart illustrating a state space approach to classification of heart beats and characterization of a physiological condition.

FIG. 5 is a flow chart illustrating a state space approach to classification of heart beats and characterization of a physiological condition. A cardiac signal can be obtained at 510. The cardiac signal can be translated into an embedding space that represents coarse-grained dynamics of the heart at 520. For example, the embedding space can be made up from multiple cardiac signals from independent leads and the Hilbert transforms of the multiple cardiac signals.

State space techniques can be employed to extract physiological information for the heart from the embedding space at 530. This can involve deriving multiple dynamical quantities from the embedding space. This can include calculating three or more dynamical measures of heart activity and derivative physiological quantities, such as speed of trajectory, length of trajectory, area integral of a speed vector and threshold crossings in state space.

Speed of trajectory in state space can be defined as a dynamical quantity V(t), calculated as:

$$\vec{V}(t) = \frac{\vec{S}(t) - \vec{S}(t - \Delta t)}{\Delta t}, \quad (1)$$

where $\vec{S}(t)$ is a vector in the state space with coordinates x(t) and H(x(t)). Length of a trajectory in state space can be defined as a dynamical quantity L(t), which can be calculated as the sum of the point to point distances in state space; this is a nonlinear function of phase trajectory, which can be used to estimate system wandering (random deviation) from expected evolution. Area integral of a speed vector can be estimated as:

$$A(t) = \sum_{t=t_0}^{t_0 + n\Delta t} |\vec{V}(t) \otimes [\vec{V}(t) - \vec{V}(t - \Delta t)]|, \quad (2)$$

where nΔt is the time interval where area A(t) is calculated. Threshold crossings in state space correspond to selected points in state space at which a trajectory crosses specific planes such as (x(t),0) or (0,H(t)). In general, intersection of phase trajectory and a selected surface is called Poincare mapping, and this mapping can be used to find onsets of state transitions, such as peaks of electrophysiological waves. Although three examples of dynamical quantities are described, it will be apparent that other state space analysis techniques can also be used, such as nearest neighbor techniques, calculation of topological defects, or variations of these.

The heart can be considered as a dynamical system, meaning that there are some deterministic (dynamical) laws governing the electrical pulses traveling through the heart tissue. Detailed reconstruction of heart dynamics is possible in theory, but often impractical because of the noise and variability in ECG data. However, for diagnostic purposes, full reconstruction is not necessary. Thus, partial reconstruction of the state space, representing coarse-grained dynamics of the heart, can be a highly effective approach to cardiac monitoring.

To illustrate this further, suppose a fully reconstructed multi-dimensional state space has been obtained. In this full state space, the reconstructed dynamics have a large amplitude when projected in some directions, and very small amplitude in other directions. By choosing a linear orthogonal transform that maximizes amplitude in two dimensions and minimizes the remaining projections, the first two dimensions represent large amplitude, coarse-grained dynamics, and other dimensions include lower amplitude, finer-grained dynamical movements. In addition, the finer-grained dimensions include noisy, less regular movements. Thus, the first two dimensions should be the most useful for diagnostic purposes because they predominantly represent dynamics of the biological system (the heart, in this example) and are less influenced by noise. Therefore, the first two dimensions can be used for diagnostic purposes. As should be appreciated in light of the above, instead of implementing a sequence of input signal->full state space->two dimensional coarse-grained state space, all that is needed is a direct transform of input signal->two dimensional coarse grained state space, which should provide substantially all the benefits of the first in a less computationally intensive procedure.

Heart beats in the sensed cardiac signal can be classified based on the extracted physiological information at 540. This can involve detecting abnormal heart beats as described above. A physiological condition can be characterized at 550. This can involve estimating a physiological condition based on detected abnormal heart beats. Such estimates or characterizations of a physiological condition can serve as a preliminary finding of a particular diagnosis for a patient.

Thus, in addition to detecting specific physiological events, such as heart beats, the present systems and techniques can be used to detect broader physiological occurrences, such as the development of a specific heart condition. This enables automated prediction of the probability of a given physiological condition and allows an automated system to propose a diagnosis for a patient. Such predictive capability can be very useful to a clinician or physician, and can be progressively improved upon as a database of physiological information is built over time.

In the context of heart monitoring, the present systems and techniques can be used to accurately identify the beginning and ending points of the heart waveforms, including P waves and U waves. This can enable more accurate calculation of physiological intervals, such as QT intervals, QS intervals, PR intervals and ST segment. Thus, an automated process employing these techniques can build a comprehensive record of heart waveform intervals for a patient, and use this record to facilitate later analysis and diagnosis of the patient's current condition. Relevant clinical information can be derived from lots of heart data, but only the most salient features of the data, as determined by an automated process, need be presented to the clinician or physician.

Figure 6:
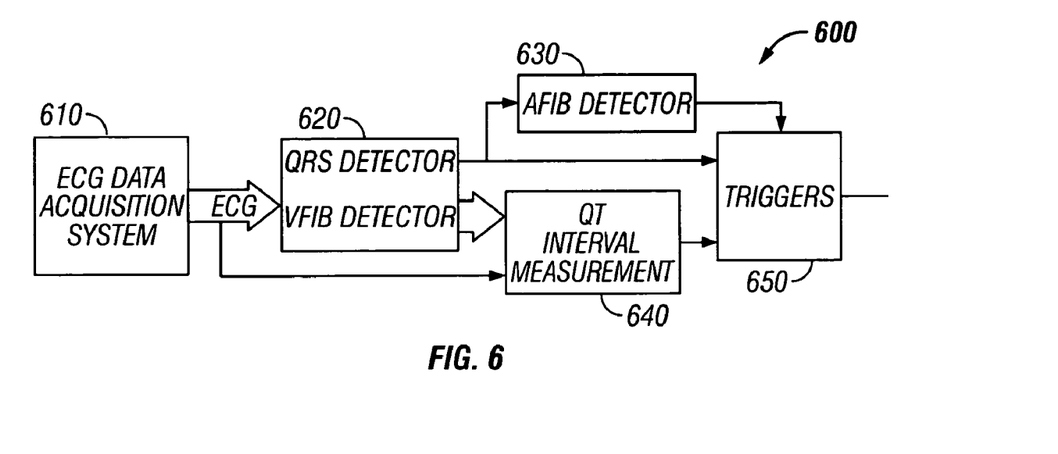
FIGS. 6 and 7 are block diagrams illustrating an example cardiac processing system and QRS detector.
Figure 7:
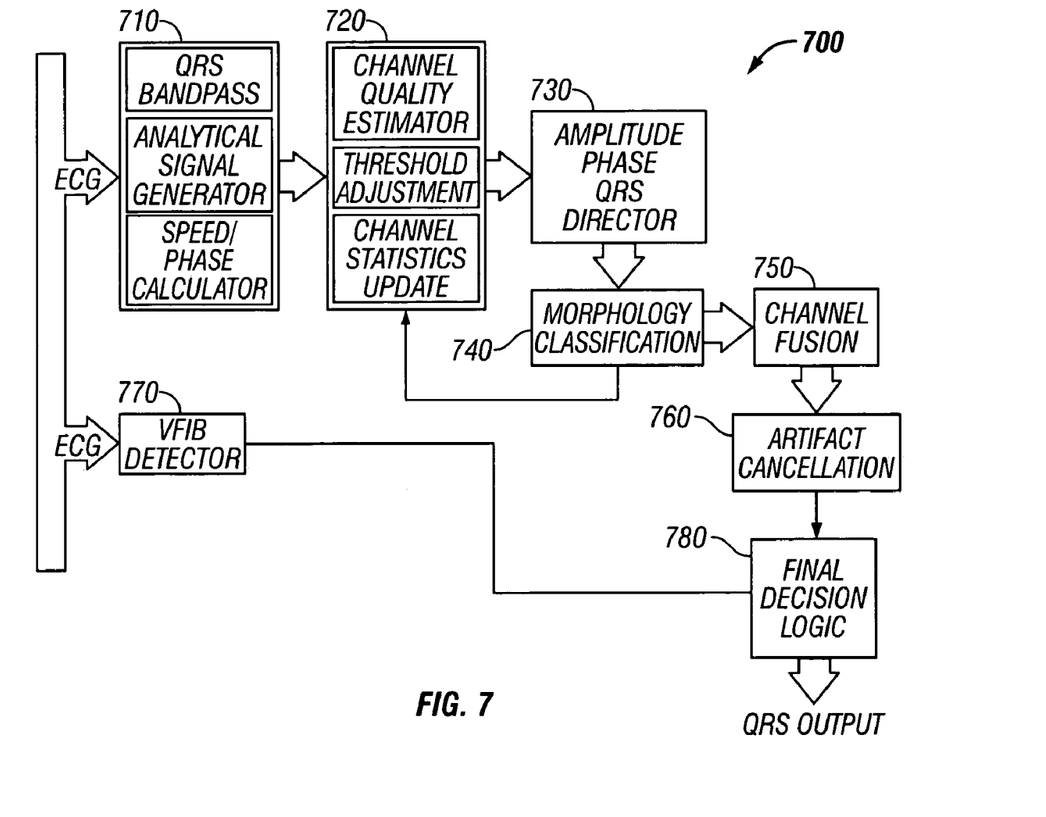

FIGS. 6 and 7 are block diagrams illustrating an example cardiac processing system 600 and QRS detector 700 employing the systems and techniques described above. The system 600 includes an ECG data acquisition system 610, which employs fewer than ten leads. For example, the system 610 can be a two lead system as described above. The ECG data acquisition system 610 can provide a two-channel sampled ECG signal to a QRS and QT analysis package for processing (e.g., at a sample rate of 250 samples/second). Moreover, the input to the package can include the sampled data, pacemaker spike and invalid lead information (per sample), plus commands and configuration information.

A QRS and VFIB (ventricular fibrillation) detector 620 can analyze the input signal and provide output including QRS location and morphology information (e.g., normal, ventricular or unclassified) and a VFIB signal. An AFIB (atrial fibrillation) detector 630 can check for atrial fibrillation. A QT interval measurement component 640 can measure the QT interval, such as described further below. Moreover, the output of these components can be provided as input to one or more triggers 650 in an arrhythmia analysis system.

Figure 8A:
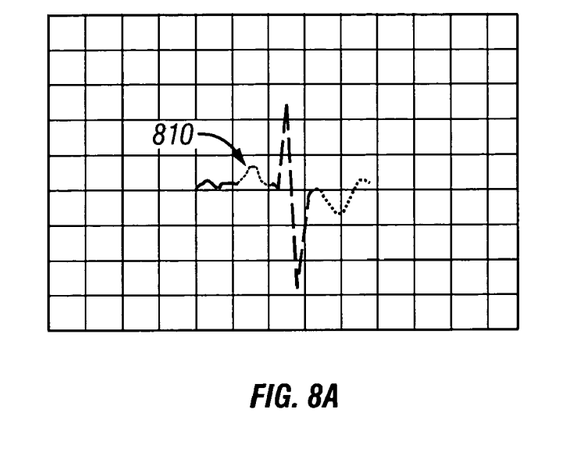
Figure 8B:
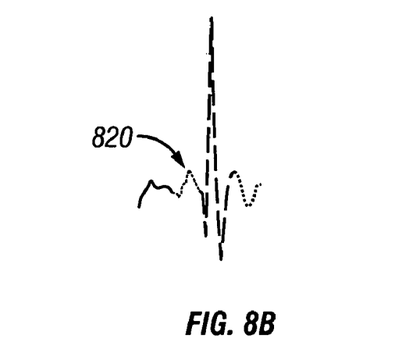
Figure 8C:
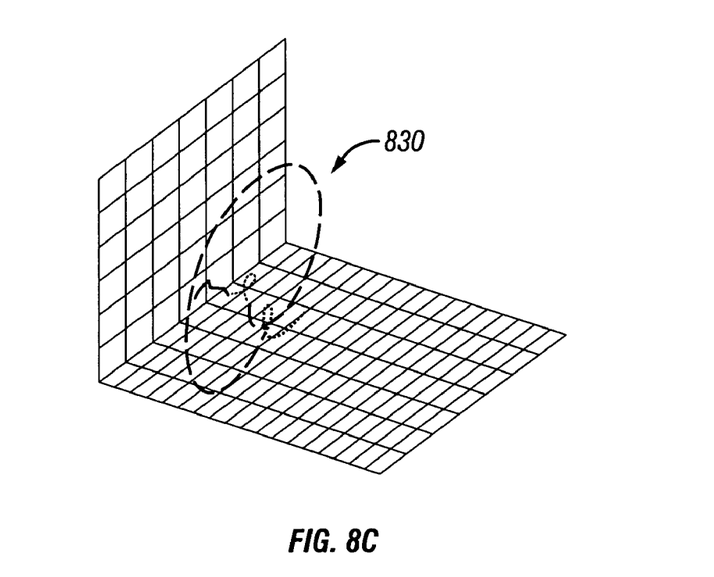

The QRS detector 700 includes a preprocessing stage 710, which can include a QRS bandpass component, an analytical signal generator and a speed/phase calculator. The preprocessing stage 710 can include a filter bank containing low and high pass filters and can construct the analytical signal as described above. For example, FIGS. 8A, 8B and 8C illustrate an original ECG signal 810, a Hilbert transform 820 of the ECG signal 810, and an analytical representation 830 of the ECG signal 810.

The preprocessing stage 710 can form a data stack used by the subsequent stages. The preprocessing stage 710 can convert incoming ECG data into a positively defined product characterizing the speed and the power of the heart's electrical activity (abbreviated below as speed-amplitude product). The preprocessing stage 710 can also provide filtered data to assist in low and high frequency noise estimation in later stages of the data analysis.

An update stage 720 can include a channel quality estimator, a threshold adjustment component, and a channel statistics update component. The channel quality estimator can report lead usability in the detection process. If one of the leads is off or not informative, the detection can be continued using the other lead. If both leads are classified by the channel quality estimator as not informative, a corresponding warning is generated.

Output of the update stage 720 can be provided to an amplitude-phase QRS detector 730. In general, QRS peak detection can involve calculation of a dynamic threshold, taking a previously detected peak as a starting point, and identification of the maximum above the threshold of the positively defined speed-amplitude product. Moreover, the detector can also be responsible for testing channel quality and adjusting itself to base line shifts and high amplitude high frequency noise. Channel quality can be estimated 250 samples (e.g., 1 second) ahead of the current sample.

A morphology classification stage 740 can employ RR' analysis (e.g., asymmetry, double notch detection), QS analysis (e.g., beat width), P-wave detection, T-wave detection and a ventricular morphology check. After successful classification, a beat can be assigned certain metrics, which can be used to update beat statistics.

A channel fusion stage 750 can make a final decision on QRS correlation between the channels, quality of the beat (beat versus artifact) and ventricular morphology. At this stage, the channels can be merged into a single output. Moreover, programmable control can be provided over the output of various information associated with the detected beat or channel quality. For example, the output can be set to include beat annotations (e.g., "N"=normal beat, "V"=ventricular beat, "Q"=not classified) and the time stamp corresponding to the detected center of the QRS complex. Extended annotations may include fiducial points (e.g., Q-points, S-points, P-wave location, and T-wave location) as well as channel characteristics (e.g., signal-to-noise ratio, detection confidence and so on).

Annotation of beats can start from the third beat detected and ventricular morphology can start from the fifth detected beat, if applicable. In general, the detector does not require learning, but in some implementations, two seconds delay may be needed for the preprocessing stage 710 to prepare filtered input and to adjust parameters. Moreover, a QRS complex can be classified as belonging to a group, and the groups can be used to update average QRS parameters to assist morphological analysis.

The QRS detector 700 can include an artifact cancellation component 760, and final decision logic 780 can generate QRS output based on input from the artifact cancellation component 760 and a VFIB detector 770. The QRS output can include a QRS-complex output for each detected QRS event. The QRS-complex output can include beat annotation and timing information. In addition, the QRS output can include QRS amplitude, QRS width and fiducial points information.

The VFIB detector 770 can detect ventricular fibrillation/flutter rhythms through analysis of the incoming ECG based on the following criteria: VFIB triggers when QRS-like activity is absent and the ventricular signal is above noise level (VFIB flag is true). If this event happens, then the QRS detector can be run in idle until the VFIB flag is set to false (VFIB is not detected).

The QRS detector 700 can also include asystole monitoring. The QRS detector 700 can use automatically adjusted thresholds. Lower limits in amplitude can be supplied as input parameters. Additionally, if a next QRS peak is not detected during ten seconds, the detector can give an asystole warning to assist external triggers.

The QT interval measurement component 640 from FIG. 7 can measure the QT interval using one of various QT interval definitions. In general, the QT interval is the distance between the Q and the end of the T-wave. The Q point is defined as the beginning of a QRS wave, but the end of the T-wave can be defined in at least two distinct ways: a "tangent" approach and an "amplitude" approach. The amplitude approach defines the end of a T wave as a point where amplitude of the ECG signal becomes less than 0.1 mV.

The tangent approach defines the end of a T wave as a point where the amplitude of an analytical signal becomes smaller than 0.1 mV. The analytical signal is an extension of the original ECG signal into the complex numbers space, such as the following:

$$A(t)=x(t)+iH(x(t)) \quad (3)$$

where H(x(t)) is a Hilbert transform of an original ECG signal x(t). A band-limited Hilbert transform (e.g., two different high-pass filters) can be used. Then, the amplitude of the analytical signal can be estimated for both representations, and the one with higher amplitude can be used for the end of T-wave calculations. The Q point can be defined as a point where amplitude of an analytical signal becomes larger than 0.1 mV. Again, a high-pass filter can be used after Hilbert transform (e.g., a high-pass filter with a cut-off frequency of 15 Hz).

It should be noted that using the tangent approach above can result in a significant reduction in the chances of underestimating the QT interval. The amplitude of the analytical signal will in general always be larger (in terms of absolute value) than the amplitude of the signal. Thus, using the tangent approach to defining the end of the T-wave can result in a few extra samples being considered part of the T-wave in some implementations. Moreover, using the tangent approach can result in consistent values being generated independent of QRS axis or an axis of a T-wave, due to the use of the analytical signal representation.

The systems and techniques described and illustrated in this specification can be implemented in analog electronic circuitry, digital electronic circuitry, integrated circuitry, computer hardware, firmware, software, or in combinations of the forgoing, such as the structural means disclosed in this specification and structural equivalents thereof (e.g., an embedded implementation). Apparatus can be implemented in a software product (e.g., a computer program product) tangibly embodied in a machine-readable medium (e.g., a storage device) for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) optical disks, such as CD-ROM disks. Any of the foregoing can be supplemented by, or incorporated in, ASICs (application-specific integrated circuits).

To provide for interaction with a user (such as the system operator), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users and operational settings can be changed in the monitoring system.

The foregoing description has been presented in terms of particular implementations. Other embodiments are within the scope of the following claims. For example, the operations can be performed in a different order and still achieve desirable results; the order of operations illustrated should not be considered limiting. Moreover, alternative implementations can use multiple physiological signals, and dynamical quantities can be based on multiple different types of physiological signals.

What is claimed is:

1. A machine-implemented method comprising:
    obtaining a physiological signal of a biological system of an organism;
    generating a transformed signal that is mathematically orthogonal to the physiological signal by applying a frequency-independent transform to the physiological signal;
    producing, from the physiological signal and the transformed signal, a partial state space representing dynamics of the biological system, the partial state space being a partial reconstruction of a state space representing system dynamics for the biological system; and
    identifying physiological information concerning the organism based on an analysis of signal morphology in the partial state space;
    wherein the producing and the identifying are performed by one or more data processing apparatus.

2. The method of claim 1, wherein obtaining the physiological signal comprises receiving a sensed cardiac signal.

3. The method of claim 2, wherein identifying the physiological information comprises classifying heart beats in the sensed cardiac signal.

4. The method of claim 2, wherein identifying the physiological information comprises characterizing a physiological condition of the organism.

5. The method of claim 1, wherein identifying the physiological information comprises detecting a physiological occurrence for the biological system based on a dynamical quantity comprising a value derived from the physiological signal and the transformed signal.

6. The method of claim 5, wherein obtaining the physiological signal comprises receiving an electrically-sensed time series x(t), generating the transformed signal comprises applying Hilbert (H) transform to the time series x(t) to obtain H(x(t)), and producing the partial state space comprises considering x(t) and H(x(t)) together as components of a state vector.

7. The method of claim 6, further comprising generating multiple dynamical quantities from the physiological signal and the transformed signal, and wherein identifying the physiological information comprises assessing the multiple dynamical quantities with respect to one or more predefined physiological aspects of the biological system.

8. The method of claim 7, wherein the multiple dynamical quantities comprise nonlinear transformations of x(t) and H(x(t)) in state space, excepting simple linear combinations of amplitude and phase.

9. The method of claim 5, wherein obtaining the physiological signal comprises receiving a real-time, electrocardiogram time series for an actively monitored human heart, generating the analytic signal comprises applying Hilbert transform directly to the received electrocardiogram time series, and detecting the physiological occurrence comprises assessing the dynamical quantity with respect to one or more predefined physiological aspects of the human heart.

10. The method of claim 1, wherein the frequency-independent transform comprises a nonlinear transform.

11. The method of claim 10, wherein the frequency-independent transform comprises a linear transform and a nonlinear transform.

12. A software product tangibly embodied in a machine-readable medium, the software product comprising instructions operable to cause data processing apparatus to perform operations comprising:
   obtaining a physiological signal of a biological system of an organism;
   generating a transformed signal that is mathematically orthogonal to the physiological signal by applying a frequency-independent transform to the physiological signal;
   producing, from the physiological signal and the transformed signal, a partial state space representing dynamics of the biological system, the partial state space being a partial reconstruction of a potential full state space for the biological system; and
   identifying physiological information concerning the organism based on an analysis of signal morphology in the partial state space.

13. The software product of claim 12, wherein obtaining the physiological signal comprises receiving a sensed cardiac signal.

14. The software product of claim 13, wherein identifying the physiological information comprises classifying heart beats in the sensed cardiac signal.

15. The software product of claim 13, wherein identifying the physiological information comprises characterizing a physiological condition of the organism.

16. The software product of claim 12, wherein identifying the physiological information comprises detecting a physiological occurrence for the biological system based on a dynamical quantity comprising a value derived from the physiological signal and the transformed signal.

17. The software product of claim 16, wherein obtaining the physiological signal comprises receiving an electrically-sensed time series x(t), generating the transformed signal comprises applying Hilbert (H) transform to the time series x(t) to obtain H(x(t)), and producing the partial state space comprises considering x(t) and H(x(t)) together as components of a state vector.

18. The software product of claim 17, the operations further comprising generating multiple dynamical quantities from the physiological signal and the transformed signal, and wherein identifying the physiological information comprises assessing the multiple dynamical quantities with respect to one or more predefined physiological aspects of the biological system.

19. The software product of claim 18, wherein the multiple dynamical quantities comprise nonlinear transformations of x(t) and H(x(t)) in state space, excepting simple linear combinations of amplitude and phase.

20. The software product of claim 16, wherein obtaining the physiological signal comprises receiving a real-time, electrocardiogram time series for an actively monitored human heart, generating the analytic signal comprises applying Hilbert transform directly to the received electrocardiogram time series, and detecting the physiological occurrence comprises assessing the dynamical quantity with respect to one or more predefined physiological aspects of the human heart.

21. The software product of claim 12, wherein the frequency-independent transform comprises a nonlinear transform.

22. The software product of claim 21, wherein the frequency-independent transform comprises a linear transform and a nonlinear transform.

23. A cardiac monitoring apparatus comprising:
   an ECG input element;
   a state space transformation component responsive to an output of the ECG input element and configured to generate a transformed signal that is mathematically orthogonal to a physiological signal, for a biological system of an organism, by applying a frequency-independent transform to the physiological signal; and
   a QRS identification component responsive to an output of the state space transformation component, the QRS identification component comprising one or more dynamical quantity calculators that each produce a value derived from a combination of the physiological signal and the transformed signal in a partial state space representing dynamics of the biological system, the partial state space being a partial reconstruction of a state space representing system dynamics for the biological system.

24. A cardiac monitoring apparatus comprising:
   an ECG input element;
   a state space transformation component responsive to an output of the ECG input element; and
   a QRS identification component responsive to an output of the state space transformation component, the QRS identification component comprising one or more dynamical quantity calculators;
   the apparatus further comprising a pQRST parameter averaging component coupled with the QRS identification component, a noise estimator responsive to the output of the ECG input element, and final QRS decision logic coupled with the QRS identification component, the pQRST parameter averaging component and the noise estimator.

25. The apparatus of claim 24, further comprising a filter coupled between the ECG input element and both the state space transformation component and the noise estimator.

26. The apparatus of claim 25, wherein the output of the ECG input element comprises a split output, the apparatus further comprising an arrhythmia identification component coupled with the split output and with an input of the final QRS decision logic.

27. The apparatus of claim 26, wherein the arrhythmia identification component comprises a ventricular fibrillation detector.

28. A system comprising:
   an ECG input element;
   a state space transformation component responsive to an output of the ECG input element and configured to generate a transformed signal that is mathematically orthogonal to a physiological signal, for a biological system of an organism, by applying a frequency-independent transform to the physiological signal;

a QRS identification component responsive to an output of the state space transformation component, the QRS identification component comprising one or more dynamical quantity calculators that each produce a value derived from a combination of the physiological signal and the transformed signal in a partial state space representing dynamics of the biological system, the partial state space being a partial reconstruction of a state space representing system dynamics for the biological system; and an antenna coupled with the QRS identification component and configured to wirelessly transmit physiological information.

29. The system of claim 28, further comprising a monitoring station configured to receive the transmitted physiological information.

30. A system comprising:
an ECG input element;
a state space transformation component responsive to an output of the ECG input element;
a QRS identification component responsive to an output of the state space transformation component, the QRS identification component comprising one or more dynamical quantity calculators;
an antenna coupled with the QRS identification component and configured to wirelessly transmit physiological information; and
a monitoring station configured to receive the transmitted physiological information,
the system further comprising a pQRST parameter averaging component coupled with the QRS identification component, a noise estimator responsive to the output of the ECG input element, and final QRS decision logic coupled with the QRS identification component, the pQRST parameter averaging component and the noise estimator.

31. The system of claim 30, further comprising a filter coupled between the ECG input element and both the state-space transformation component and the noise estimator.

32. The system of claim 31, wherein the output of the ECG input element comprises a split output, the apparatus further comprising an arrhythmia identification component coupled with the split output and with an input of the final QRS decision logic.

33. The system of claim 32, wherein the arrhythmia identification component comprises a ventricular fibrillation detector and an asystole detector.

34. A machine-implemented method comprising:
obtaining a cardiac signal of a heart;
translating the cardiac signal into an embedding space that represents coarse-grained dynamics of the heart, said translating comprising applying Hilbert transform to the cardiac signal; and
employing state space analysis techniques to extract physiological information for the heart from the embedding space;
wherein the translating and the employing are performed by one or more data processing apparatus.

35. The method of claim 34, wherein obtaining the cardiac signal comprises obtaining multiple cardiac signals from independent leads, and translating the cardiac signal comprises applying the Hilbert transform directly to the multiple cardiac signals to form the embedding space having an embedding dimension greater than or equal to twice a number of the independent leads.

36. The method of claim 35, wherein the number of the independent leads is two, and the embedding space has four spatial dimensions.

37. The method of claim 35, wherein obtaining the multiple cardiac signals comprises retrieving the multiple cardiac signals from a database.

38. The method of claim 34, wherein translating the cardiac signal comprises calculating a nonlinear combination of the cardiac signal and the Hilbert transform of the cardiac signal.

39. The method of claim 34, wherein employing state space analysis techniques comprises deriving multiple dynamical quantities from the embedding space.

40. The method of claim 39, wherein the multiple dynamical quantities comprise speed of trajectory in state space, length of trajectory in state space, area integral of a speed vector, and threshold crossings in state space.

41. The method of claim 34, further comprising detecting abnormal heart beats based on the extracted physiological information.

42. The method of claim 41, further comprising estimating a physiological condition based on the detected abnormal heart beats.

43. A software product tangibly embodied in a machine-readable medium, the software product comprising instructions operable to cause one or more data processing apparatus to perform operations comprising:
obtaining a cardiac signal of a heart;
translating the cardiac signal into an embedding space that represents coarse-grained dynamics of the heart, said translating comprising applying Hilbert transform to the cardiac signal; and
employing state space analysis techniques to extract physiological information for the heart from the embedding space.

44. The software product of claim 43, wherein obtaining the cardiac signal comprises obtaining multiple cardiac signals from independent leads, and translating the cardiac signal comprises applying the Hilbert transform directly to the multiple cardiac signals to form the embedding space having an embedding dimension greater than or equal to twice a number of the independent leads.

45. The software product of claim 44, wherein the number of the independent leads is two, and the embedding space has four spatial dimensions.

46. The software product of claim 44, wherein obtaining the multiple cardiac signals comprises retrieving the multiple cardiac signals from a database.

47. The software product of claim 43, wherein translating the cardiac signal comprises calculating a nonlinear combination of the cardiac signal and the Hilbert transform of the cardiac signal.

48. The software product of claim 43, wherein employing state space analysis techniques comprises deriving multiple dynamical quantities from the embedding space.

49. The software product of claim 48, wherein the multiple dynamical quantities comprise speed of trajectory in state space, length of trajectory in state space, area integral of a speed vector, and threshold crossings in state space.

50. The software product of claim 43, the operations further comprising detecting abnormal heart beats based on the extracted physiological information.

51. The software product of claim 50, the operations further comprising estimating a physiological condition based on the detected abnormal heart beats.

* * * * *